(12) United States Patent
Vongsurakrai et al.

(10) Patent No.: US 9,050,355 B2
(45) Date of Patent: Jun. 9, 2015

(54) METHOD FOR PRODUCING COSMETIC AND/OR DERMATOLOGICAL POWDER

(75) Inventors: Varatus Vongsurakrai, Bangkoknoi (TH); Saiyavit Varavinit, Bangkok (TH)

(73) Assignee: Dr. Varatus Vongsurakrai, Bangkhunon, Bangkok (TH)

( * ) Notice: Subject to any disclaimer, the term of this patent is extended or adjusted under 35 U.S.C. 154(b) by 936 days.

(21) Appl. No.: 11/958,765

(22) Filed: Dec. 18, 2007

(65) Prior Publication Data
US 2009/0155319 A1    Jun. 18, 2009

(51) Int. Cl.
| *A61K 8/02* | (2006.01) |
| *A61K 8/891* | (2006.01) |
| *A61K 8/73* | (2006.01) |
| *A61K 31/718* | (2006.01) |
| *A61K 9/14* | (2006.01) |
| *A61Q 19/00* | (2006.01) |
| *A61K 47/02* | (2006.01) |
| *A61K 47/36* | (2006.01) |

(52) U.S. Cl.
CPC ............... *A61K 31/718* (2013.01); *A61K 8/02* (2013.01); *A61K 8/732* (2013.01); *A61K 8/891* (2013.01); *A61K 9/146* (2013.01); *A61K 47/02* (2013.01); *A61K 47/36* (2013.01); *A61K 2800/31* (2013.01); *A61Q 19/00* (2013.01)

(58) Field of Classification Search
CPC ..... A61K 8/732; A61K 31/718; A61K 47/36; A61K 8/891
See application file for complete search history.

(56) References Cited

U.S. PATENT DOCUMENTS

| 4,014,995 | A | * | 3/1977 | Juliano et al. .................. 514/783 |
| 5,411,750 | A | * | 5/1995 | Lajoie et al. ................... 424/717 |
| 5,871,756 | A | * | 2/1999 | Jeffcoat et al. ................ 424/401 |
| 6,080,424 | A | * | 6/2000 | Avalle ........................... 424/450 |
| 6,129,906 | A | * | 10/2000 | Steventon ........................ 424/49 |
| 6,294,180 | B1 | * | 9/2001 | Demars et al. ................. 424/401 |
| 6,416,751 | B1 | * | 7/2002 | Roulier et al. ................... 424/69 |
| 2005/0181067 | A1 | * | 8/2005 | Yokoyama et al. ............ 424/641 |
| 2006/0286048 | A1 | * | 12/2006 | Morrison et al. ............... 424/63 |

* cited by examiner

*Primary Examiner* — Rachael E Bredefeld

(74) *Attorney, Agent, or Firm* — Merchant & Gould P.C.

(57) ABSTRACT

A cosmetic or dermatological powder, which comprises (i) from 61 to 99.99% by weight is relative to the total weight of the powder of at least one starch modified by a combination of esterification and heat-moisture treatment, (ii) from 0.01 to 29.99% by weight is relative to the total weight of the powder, of an oily phase comprising at least one oil.

6 Claims, No Drawings

METHOD FOR PRODUCING COSMETIC AND/OR DERMATOLOGICAL POWDER

BACKGROUND OF THE INVENTION

1. Field of the Invention

The present invention relates to a cosmetic or dermatological powder containing at least one Aluminium Starch Octenyl Succinate, to a process for its manufacture and to a composition containing it. More particularly, the invention relates to the use of the powder or of the composition for the care and/or treatment of the skin, mucous membranes and/or the scalp, as well as for the treatment of skin disorders.

2. Description of the Background

Compositions containing Aluminium Starch Octenyl Succinate, which are useful for their beneficial effects on the skin, are known in cosmetics and dermatology. Certain modified starch makes it possible, in particular, to treat problems of sensitive skin. Moreover, it is known that the incorporation of Aluminium Starch Octenyl Succinate into cosmetic or dermatological compositions providing excellent water repellant, fat & oil absorbency, skin asperity and friction reduction properties, which is suitable for human skin.

SUMMARY OF THE INVENTION

Briefly, this object and other objects of the present invention as hereinafter will become more readily apparent can be attained by a cosmetic or dermatological powder, which comprises (i) from 61 to 99.99% by weight relative to the total weight of the powder, of at least one starch modified by a combination of esterification and heat-moisture treatment, (ii) from 0.01 to 29% by weight relative to the total weight of the powder, of an oily phase comprising at least one oil and a preservative.

DETAILED DESCRIPTION OF THE PREFERRED EMBODIMENTS

The term "powder" in this invention means a solid substance divided into very fine, homogeneous particles or grains. The powder of the invention is preferably low protein flour which contain at the maximum of 10.0% protein.

In one specific embodiment of the invention the powder comprises from 61 to 99.99% by weight relative to the total weight of the powder of at least one modified starch, and from 0.01 to 29% by weight relative to the total weight of the powder of an oily phase comprising at least one oil and a preservative.

The cosmetic or dermatological powder of the invention comprises an oily phase fixed in the modified starch. This powder in particular has the advantages of water repellant, fat & oil absorbency, skin asperity and friction reduction properties, which is suitable for human skin. Moreover, the powder of the invention is not sensitive to moisture or to bacteriological contamination. In addition, since this powder can be obtained without any emulsifier and since it keeps well, it is possible to avoid the addition of emulsifiers and/or preserving agents, and thus to obtain a powder which is much less of an irritant than the conventional skin care products.

In addition, the cosmetic product of the invention allows the incorporation of compounds therein which have different physicochemical properties. This product can thus comprise detergents. This makes it possible, in particular, to cleanse the skin while at the same time moisturizing and nourishing the skin. In fact, the present invention represents a significant contribution to the art since it provides a multipurpose cosmetic or dermatological product which is not specific to one skin type.

The powder of the invention has a particle size or number-average particle size which can range in particular from about 0.1 to 100 micron, preferably from 0.5 to 50 micron, preferably from 1 to 10 micron, this particle size being measured using a Malvern Laser Particle Size Analyzer.

The modified starch employed in the powder of the invention can be modified by a combination of esterification and heat-moisture treatment. More specifically, these reactions can be conducted in the following manner:

Esterification in an alkaline medium using octenyl succinic anhydride in order to graft functional groups, in particular octenylsuccinic, onto the starch and follow by the addition of aluminium sulfate to form Aluminium Starch Octenyl Succinate. The modified starch suspension is washed with water by the hydrocyclones or separators in order to eliminate the excess octenyl succinic anhydride and aluminium sulfate, dewatered by filter press, centrifuge, or plain vacuum belt press and dried by paddle drier at lower temperature (not over 80° C.) to 27% moisture content. The modified starch is then heated to the temperature not lower than 121° C., which is called "Heat/Moisture-Treatment" in parallel with sterilization, to dryness.

Suitable chemical modified starches which can be used of the invention, include, for example, starches esterified with octenylsuccinic anhydride, and more particularly "Aluminium Starch octenyl succinate" and followed by a physical modification namely "Heat/Moisture-Treatment" (HMT). HMT process provides completely of the water repellant property of the aluminium starch octenyl succinate.

EXAMPLE

Example 1

Skin Care Powder

Sterilized modify-starch 99.99% and Silicone oil 0.01%

Procedure

A mixture containing 99.99% of sterilized modify-starch and 0.01% of the silicone oil with fragrance is incorporated to the starch by spraying.

The powder can be used in its existing, non-reconstituted form, and constitutes a product which is effective for sensitive skin, irritated skin and greasy skin. Furthermore, the powder has the advantage of providing excellent water repellant, fat & oil absorbency, skin asperity and friction reduction properties, which is suitable for human skin.

What is claimed as new and intended to be secured by Letters Patent is:

1. A cosmetic or dermatological powder, comprising:
   99.99% by weight relative to the total weight of the powder of a starch modified by esterification, followed by heat-moisture treatment to obtain starch with excellent water repellent property, and
   about 0.01% by weight silicone oil relative to the total weight of the powder.

2. The powder according to claim 1, wherein the modified starch is an aluminum salt of the reaction of 1-octenylsuccinic anhydride and starch.

3. The powder according to claim 1, wherein the modification by heat-moisture treatment includes heating to a temperature not lower than 121 degrees C., at a moisture content not over 27%.

4. A method for making a cosmetic or dermatological powder with excellent water repellant property, comprising:
(a) chemically modifying a starch by esterification;
(b) after the step in (a), physically modifying the starch by heat-moisture treatment; and
(c) constituting a cosmetically or dermatologically suitable power with 99.99% by weight relative to the total weight of the powder of the chemically and physically modified starch and about 0.01% by weight silicone oil relative to the total weight of the powder.

5. The method according to claim 4, wherein the starch is an aluminum salt of the reaction of 1-octenylsuccinic anhydride and starch.

6. The method according to claim 4, wherein the physical modification by heat-moisture treatment includes heating to a temperature not lower than 121 degrees C., at a moisture content not over 27%.

* * * * *